United States Patent [19]

Gray et al.

[11] 3,931,147

[45] Jan. 6, 1976

[54] WATER-SOLUBLE DERIVATIVES OF SODIUM MANNOHEPTONATE

[75] Inventors: Kenneth R. Gray; John C. Steinberg, both of Shelton, Wash.

[73] Assignee: International Telephone and Telegraph Corporation, New York, N.Y.

[22] Filed: Sept. 10, 1973

[21] Appl. No.: 395,627

[52] U.S. Cl............... 260/209 R; 71/1; 71/27; 252/8.55; 260/234 R
[51] Int. Cl.² ........................................... C07H 3/02
[58] Field of Search ............... 260/209 R, 210 R

[56] References Cited
UNITED STATES PATENTS

| | | | |
|---|---|---|---|
| 3,074,927 | 1/1963 | Saltman et al. | 260/209 R |
| 3,466,252 | 9/1969 | Prahl et al. | 260/209 R |
| 3,563,978 | 2/1971 | Ochs | 260/209 R |
| 3,629,229 | 12/1971 | Schmank | 260/209 R |
| 3,679,659 | 7/1972 | Zak | 260/209 R |
| 3,706,545 | 12/1972 | Gray | 71/27 |

*Primary Examiner*—Johnnie R. Brown
*Attorney, Agent, or Firm*—James B. Raden; Harold J. Holt

[57] ABSTRACT

Water-soluble metal complexes of sodium mannoheptonate in which the metal is an aluminum, iron or chromium trivalent ion. The water-soluble complexes are produced by reacting a water slurry of sodium mannoheptonate with a salt of the trivalent metal. The reaction products are useful for inhibiting the swelling and dispersion of clays and, in the case of the iron complex, as anti-chlorotic agents for the treatment of trees and plants.

3 Claims, No Drawings

WATER-SOLUBLE DERIVATIVES OF SODIUM MANNOHEPTONATE

This invention relates to water-soluble derivatives of sodium mannoheptonate, to a process for their preparation and to their use as anti-chlorotic agents and for inhibition of the swelling of clay.

Sodium mannoheptonate is a known derivative of mannose. It shares with other mannose derivatives a high degree of insolubility in water, 2.5% at room temperature. This has considerably restricted utilization of the compound. It would therefore be desirable to provide this compound in a soluble form.

We have now discovered that chelates of sodium mannoheptonate with the three trivalent metals, aluminum, iron and chromium, are highly soluble in water. The chelate is made by reacting the sodium mannoheptonate with a salt of the trivalent metal. The solubility of this metal complex or chelate is particularly unexpected because both the salts of the trivalent metals, at alkaline pH's, as well as sodium mannoheptonate itself are essentially water insoluble. Heavy metal salts of sulfates are normally insoluble at alkaline pH's because of the formation of insoluble hydroxides. Thus, when a ferric sulfate solution is made alkaline, ferric hydroxide is precipitated. At a pH of 8, the ferric chelate of sodium mannoheptonate is far more soluble in water than either sodium mannoheptonate alone or ferric iron alone, the two reactants from which it is prepared. Moreover, highly water-soluble derivations of sodium mannoheptonate are not formed with salts of bivalent metals. Thus, attempts to prepare a soluble derivatives of sodium mannoheptonate with ferrous sulfate at alkaline pH have been unsuccessful. The iron immediately forms insoluble material — either the hydroxide mixed with sodium mannoheptonate or a ferrous salt of the mannoheptonate.

The high solubility of the three new trivalent metal chelates of sodium mannoheptonate has considerable significance, not only with reference to the utilization of sodium mannoheptonate, but also in the provision of an economical process for manufacturing chelates. The latter results from the ability to spray dry concentrated solutions of the metal complex of the invention, thus reducing drying, packaging and shipping costs of the product. All three metal complexes have been found to be useful for inhibiting the swelling of bentonite clays, iron and aluminum being most effective for this purpose. The iron complex had also been found useful for correction of iron deficiency in trees and plants.

The sodium mannoheptonate derivatives of the invention are accurately defined as either metal complexes or chelates and the terms are used herein interchangeably with reference to these derivatives. Both terms describe derivatives in which the metal is held by coordinate bonding.

Sodium mannoheptonate may be prepared by a cyanohydrin reaction with mannose. Mannose itself is an article of commerce, available from a number of natural sources such as plant materials. In the process of the present invention, from one half to one mole of the trivalent metal salt is reacted with a water slurry of one mole of sodium mannoheptonate. In some cases, particularly with the ferric complex, the slurry is highly acidic after reaction is complete and the slurry should desirably be adjusted to a pH of 5.0 or higher. The reaction product may thereafter be spray dried to form a powder of the trivalent metal complex. A suitable salt is aluminum, iron or chromium sulfate, although other salts, including but not limited to, chlorides or other halides, nitrates, acetates and other water-soluble salts may be used.

The following examples illustrate the practice of the present invention.

EXAMPLE 1

In this example, the sodium mannoheptonate product (SMH) used contained, by analysis, 92.0% sodium mannoheptonate (i.e., sodium-D-glycero-D-gala-heptonate), on a dry basis, and 7.0% moisture on a wet basis.

A slurry comprising 117 grams of SMH and 300 grams of water was prepared. To this slurry was added 99.5 grams of hydrated ferric sulfate (81% anhydrous).

The resulting mixture was (1) heated to 150°F. and retained at that temperature for 30 minutes with stirring, (2) adjusted from pH 1.5 to pH 8.0 by the addition of 85.0 grams of 48.7% NaOH solution and (3) spray dried using 600°F. drying air. The dried product, containing 1.0 moles ferric iron per mole of carboxyl in the SMH, was designated Product A.

EXAMPLE 2

The procedure of Example 1 was repeated except that 52.7 grams of hydrated chromic sulfate (75% anhydrous), rather than ferric sulfate, was added to the SMH slurry. Following the 30 minute retention period at 150°F., the mixture was adjusted from pH 3.1 to pH 8.0 by the addition of 25.0 grams of 48.7% NaOH solution. The spray dried product, containing 0.5 moles chromium per mole of carboxyl in the SMH, was designated Product B.

EXAMPLE 3

The procedure of Example 1 was repeated except that 134.4 grams of hydrated aluminum sulfate (55.2% anhydrous), rather than ferric sulfate, was added to the SMH slurry. Following the 30 minute retention at 150°F., the mixture was adjusted from pH 3.0 to pH 8.0 by the addition of 93.0 grams of 48.7% NaOH solution. The spray dried product, containing 1.07 moles aluminum per mole of carboxyl in the SMH, was designated Product C.

Solubility tests were conducted with Products A, B and C of Examples 1, 2 and 3. In addition, for purposes of comparison, a product was prepared using a bivalent metal salt. The procedure described in Example 1 was repeated except that 112 grams $FeSO_4 \cdot 7H_2O$, rather than ferric sulfate, was added to the SMH slurry. Following the 30 minute retention at 150°F., the mixture was adjusted from pH 6.1 to pH 8.0 by the addition of 18.0 grams of 48.7% NaOH solution. The spray dried product, containing 1.0 moles ferrous iron per mole of carboxyl in the SMH, was designated Product D. Products A, B, C and D were each mixed with water, adjusted to pH 8.0 with 48.7% NaOH solution and allowed to stand overnight. The solubility of each product was then observed. A pH of 8 was used because it is a pH at which the hydroxides normally begin precipitating and, in addition, is approximately the pH found in drilling muds, where the present products find an important application. The solubility results are set forth in Table I.

Table I

| Product | Weight, grams Product | Water | 48.7% NaOH | Product Conc., % | Product Solubility |
|---|---|---|---|---|---|
| SMH | 20 | 80 | Trace | 20.0 | Very slight soluble. |
| $Fe_2(SO_4)_3$ | 7 | 85 | 9 | 6.9 | Formed a reddish-brown insoluble precipitate ($Fe(OH)_3$). |
| A | 20 | 80 | None | 20.0 | Completely soluble, forming a dark brown solution. |
| B | 20 | 80 | Trace | 20.0 | Completely soluble, forming a dark brown solution. |
| C | 20 | 80 | None | 20.0 | Completely soluble, forming a light brown, somewhat opalescent solution. |
| D | 10 | 90 | Trace | 10.0 | Substantially insoluble, forming a bluish-green slurry. |

Table I shows that the trivalent metal complexes of SMH (Products A, B and C) are completely soluble at 20% concentration and a pH of 8 whereas at the same pH, the individual components from which the metal complexes were prepared are substantially insoluble (SMH) or decompose ($Fe_2)SO_4)_3$) to form an insoluble product. In addition a bivalent metal salt (Product D) does not produce a soluble metal complex.

EXAMPLE 4

In order to test the use of the ferric metal complex of the invention as an anti-chlorotic agent, the following experiment was conducted. Limbs of three pear trees in an orchard near Wenatchee, Washington were selected with pronounced chlorosis symptions (yellowing of leaves with veins remaining green) so that each treatment could be applied to a limb end 12 to 18 inches in length. Leaves behind this section of the limb were also chlorotic and were used for comparison in addition to control limbs which were untreated. The spray solutions were made up to contain 1270 ppm iron and 0.01% Aerosol OT, a wetting agent. The sprays were applied on June 1, and observation made August 13, with the following results. On the control branches, chlorosis correction was from zero to a maximum of 20% and there was some die-back that is, dying of the tip of the branch. The treatment with the ferric complex of sodium mannoheptonate resulted in a correction of up to 70% of the chlorosis and there was no die-back.

EXAMPLE 5

Additional tests were conducted to determine the utility of the metal complexes of the invention on the swelling of clay in water. 6 grams of the product were dissolved in 300 ml. of distilled water, and the pH of the solution was adjusted to 10.5 with sodium hydroxide. 30 grams of sodium bentonite were then added and the mixture was bottled and rolled 16 hours at 70°C. Viscosity and gel strengths were then determined using a Fann model 35 viscometer. The results are set forth in Table II. Lowered viscosity and gels indicate decreased swelling and viscosity building.

Table II

| Complexing Metal | Mol Ratio, metal to ligand | Aged pH | Viscosity cp | Gel Strength lb./100 sq.ft. o min. | 10 min. |
|---|---|---|---|---|---|
| No treatment | | 8.3 | 64 | 49 | 71 |
| Iron | 0.5 | 7.7 | 16 | 2 | 4 |
| Iron | 1.0 | 7.9 | 11.5 | 1 | 1 |
| Aluminum | 0.5 | 8.9 | 9 | 1 | 1 |
| Aluminum | 1.1 | 9.4 | 6 | 1 | 1 |

It is thus seen that the metal complexes result in pronounced reduction of the viscosity and swelling characteristics of the dispersion of clay in water. The chromium complex was tested and also demonstrated effectiveness for inhibiting swelling of sodium bentonite clays.

We claim:

1. A water-soluble metal complex of sodium mannoheptonate in which the metal is selected from the group consisting of aluminum, and chromium trivalent ions.

2. The metal complex of claim 1 in which the metal is aluminum.

3. The metal complex of claim 1 in which the metal is chromium.

* * * * *